(12) United States Patent
Denpou et al.

(10) Patent No.: US 6,306,473 B1
(45) Date of Patent: Oct. 23, 2001

(54) MULTILAYER FILM AND CONTAINER

(75) Inventors: Takayuki Denpou; Tamotsu Kataoka, both of Naruto; Keiichi Hattori, Tokushima, all of (JP)

(73) Assignee: Otsuka Pharmaceutical Factory Inc., Tokushima (JP)

( * ) Notice: Subject to any disclaimer, the term of this patent is extended or adjusted under 35 U.S.C. 154(b) by 0 days.

(21) Appl. No.: 09/462,849

(22) PCT Filed: Jul. 6, 1998

(86) PCT No.: PCT/JP98/03044

§ 371 Date: Jan. 14, 2000

§ 102(e) Date: Jan. 14, 2000

(87) PCT Pub. No.: WO99/03679

PCT Pub. Date: Jan. 28, 1999

(30) Foreign Application Priority Data

Jul. 17, 1997  (JP) .................................................... 9-192765

(51) Int. Cl.$^7$ ............................ B32B 27/32; B65D 65/40; A61J 1/05
(52) U.S. Cl. .......................... 428/35.2; 428/213; 428/218; 428/220; 428/515; 428/516
(58) Field of Search ................................... 428/35.2, 212, 428/213, 218, 219, 220, 515, 516

(56) References Cited

U.S. PATENT DOCUMENTS 5,300,353   4/1994   Yoshimura et al. .................. 428/213
5,783,269   7/1998   Heilmann et al. ................... 428/35.2

FOREIGN PATENT DOCUMENTS

| | | |
|---|---|---|
| 0 634 270 | 1/1995 | (EP) . |
| 0 635 254 | 1/1995 | (EP) . |
| 0 698 487 | 2/1996 | (EP) . |
| 0 699 521 | 3/1996 | (EP) . |
| 0 705 687 | 4/1996 | (EP) . |
| 0 739 713 | 10/1996 | (EP) . |
| 62-64363 | 3/1987 | (JP) . |
| 63-248633 | 10/1988 | (JP) . |
| 3-277365 | 12/1991 | (JP) . |
| 4-266759 | 9/1992 | (JP) . |

OTHER PUBLICATIONS

Derwent Abstracts of JP 7–136234 for "Medical Multilayer Film of Good Transparency, Flexibilty, Impact Resistance, etc."(1995).

*Primary Examiner*—D. S. Nakarani
(74) *Attorney, Agent, or Firm*—Finnegan, Henderson, Farabow, Garrett & Dunner L.L.P.

(57) ABSTRACT

The present invention provides a multilayer film comprising five layers, wherein each layer is constituted by a resin having the following density in that order. 1st layer an ethylene α-olefin copolymer having a density of 0.930 to 0.950 g/cm$^3$, 2nd layer: an ethylene-α-olefin copolymer having a density of 0.890 to 0.920 g/cm$^3$, 3rd layer a polypropylene having a density of 0.900 to 0.930 g/cm$^3$, 4th layer: an ethylene-α-olefin copolymer having a density of 0.890 to 0.920 g/cm$^3$, and 5th layer an ethylene-α-olefin copolymer having a density of 0.915 to 0.950 g/cm$^3$, and a container using the same. This container is useful for containing liquid medicine, blood or the like in the medical field.

10 Claims, 3 Drawing Sheets

F I G. 3
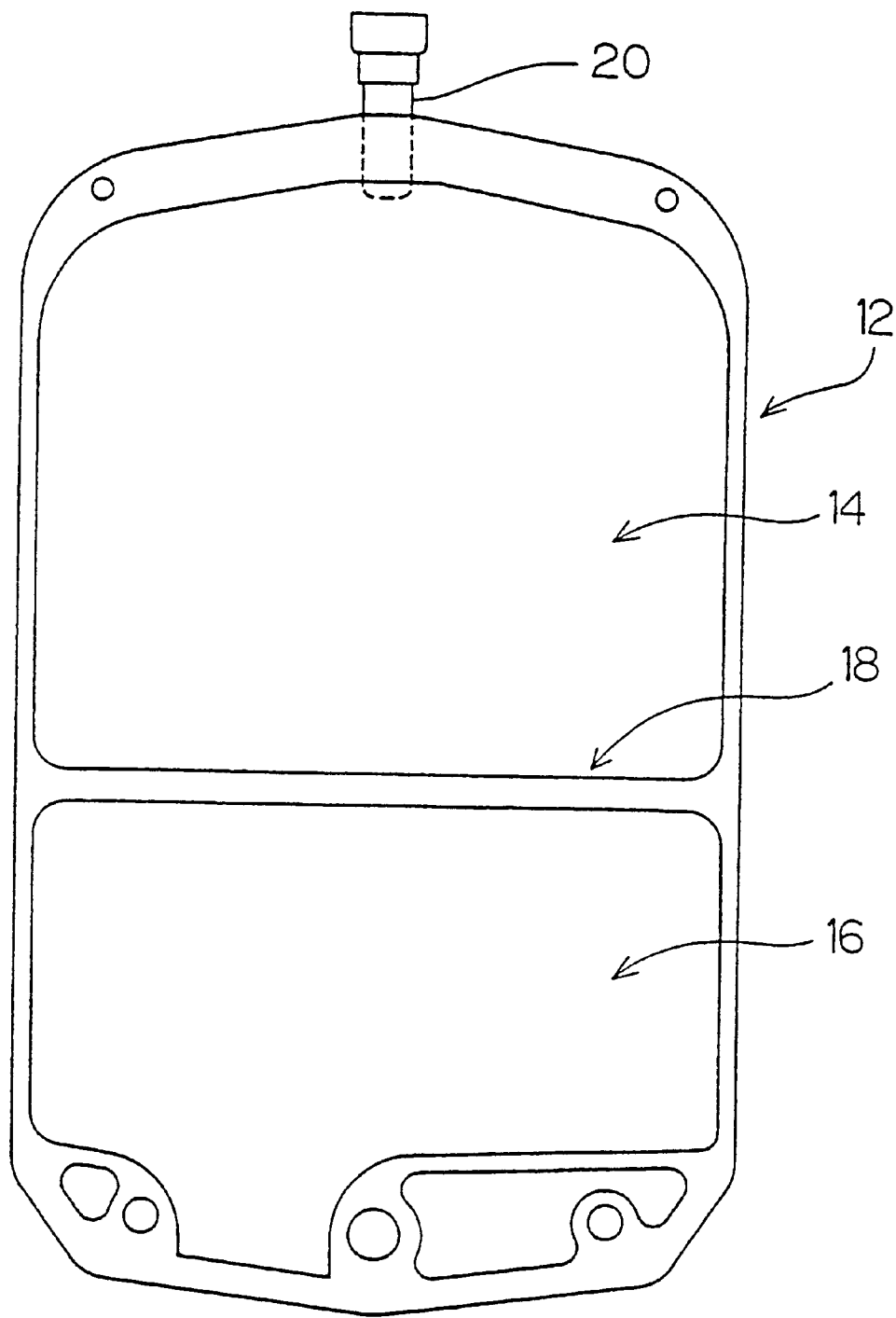

MULTILAYER FILM AND CONTAINER

TECHNICAL FIELD

The present invention relates to a multilayer film, and a container molded by using the same. More particularly, it relates to a multilayer film used as a material for containing liquid medicine, blood or the like in the medical field, and a container.

BACKGROUND ART

Regarding a medical flexible plastic container such as infusion fluid bag, a trial of using a multilayer film as a raw material has been made to improve its properties.

Examples of a conventional medical multilayer container include those of the following polyethylene resins.

*Japanese Kokai (Laid-Open) Patent Publication No. 62-64363*

A three-layer bag of a linear low-density polyethylene, wherein each density of outer and inner layers is not less than 0.920 g/cm$^3$ and a density of an intermediate layer is less than 0.920 g/cm$^3$

*Japanese Patent Kokai (Laid-Open) Publication No. 63-248633*

A three-layer container of a linear low-density polyethylene, wherein each density of outer and inner layers is from 0.910 to 0.940 g/cm$^3$, a density of an intermediate layer is from 0.880 to 0.905 g/cm$^3$, and a difference in density between them is not less than 0.01 g/cm$^3$

*Japanese Patent Kokai (Laid-Open) Publication No. 3-277365*

A three-layer bag comprising an outer layer of a linear low-density polyethylene having a density of not less than 0.920 g/cm$^3$, an intermediate layer of a linear low-density polyethylene having a density of not more than 0.915 g/cm$^3$ and an inner layer of a branched low-density polyethylene having a density of not less than 0.918 g/cm$^3$

*Japanese Patent Kokai (Laid-Open) Publication No. 4-266759*

A bag of three or more layers, comprising inner and outer layers of a resin obtained by mixing a long-chain branched low-density polyethylene having a density of not more than 0.930 g/cm$^3$ with 5–40% of a high-density polyethylene having a density of not less than 0.945 g/cm$^3$, and an intermediate layer of a resin obtained by mixing a linear low-density polyethylene having a density of not more than 0.920 g/cm$^3$ with not more than 15% of the above high-density polyethylene.

However, the above conventional medical multilayer container has any one of the following drawbacks.

(1) Since the inner and outer layers are composed with a low-density polyethylene resin, the heat resistance is not sufficient and the sealing strength and drop strength are lowered as a result of sterilization under high-temperature conditions, such as high-pressure steam sterilization, hot-water sterilization or the like.

(2) After the above sterilization under high-temperature conditions, blocking is liable to arise (low blocking resistance).

(3) Since the strength of the film is low, it is necessary to increase the wall thickness.

(4) Since the tensile strength is not sufficient, the rate of producing bags can not be increased.

(5) Since the temperature of a heater can not be increased at the time of heat sealing, sealing can not be performed in a short time (sealability is poor).

(6) The transparency and flexibility are lowered after sterilization.

When a medical container (infusion fluid bag) 10 as shown in FIG. 1 is produced, two films 22, 22 are piled up each other and peripheries of films 22, 22 are heat sealed in the state where a port member (port) 20 it inserted between the films.

However, as shown in FIG. 2, since the film 22 bends largely at the portion adjacent to the port member 20, when a conventional multilayer film is heat-sealed, the film is stretched at the bending portion 24 and the film thickness is reduced. Therefore, pinhole is liable to arise.

DISCLOSURE OF THE INVENTION

It is an object of the present invention to provide a multilayer film, which is superior in heat resistance, blocking resistance, strength, sealability, transparency, flexibility and appearance, and is capable of preventing pinhole from arising at the bending portion at the time of heat sealing, and a container.

The present inventors have intensively studied to accomplish the above object. As a result, the present invention has been completed.

That is, the present invention relates to the followings:

(1) A multilayer film comprising five layers, wherein each layer is constituted by a resin having the following density in that order:

1st layer: an ethylene-α-olefin copolymer having a density of 0.930 to 0.950 g/cm$^3$, 2nd layer: an ethylene-α-olefin copolymer having a density of 0.890 to 0.920 g/cm$^3$, 3rd layer: a polypropylene having a density of 0.900 to 0.930 g/cm$^3$, 4th layer: an ethylene-α-olefin copolymer having a density of 0.890 to 0.920 g/cm$^3$, and 5th layer: an ethylene-α-olefin copolymer having a density of 0.915 to 0.950 g/cm$^3$;

(2) The multilayer film according to the above item (1), wherein the resin used in the 5th layer is a mixed resin obtained by mixing an ethylene-α-olefin copolymer having a density of 0.915 to 0.950 g/cm$^3$ with a polypropylene having a density of 0.900 to 0.930 g/cm$^3$ in a weight ratio of 1:3 to 9:1;

(3) The multilayer film according to the above item (1), wherein the resin used in the 3rd layer is a mixed resin obtained by mixing a polypropylene having a density of 0.900 to 0.930 g/cm$^3$ with not more than 60% by weight of an ethylene-α-olefin copolymer having a density of 0.860 to 0.930 g/cm$^3$;

(4) The multilayer film according to the above item (3), wherein the resin used in the 3rd layer is a mixed resin obtained by mixing a polypropylene having a density of 0.900 to 0.930 g/cm$^3$ with 5–20% by weight of an ethylene-α-olefin copolymer having a density of 0.860 to 0.930 g/cm$^3$;

(5) The multilayer film according to any one of the above items (1) to (4), wherein the resin used in the 2nd layer and 4th layer is a mixed resin comprising 30–60% by weight of an ethylene-α-olefin copolymer having a density of 0.910 to 0.930 g/cm$^3$, 35–65% by weight of an ethylene-α-olefin copolymer having a density of 0.860 to 0.900 g/cm$^3$ and 1–10% by weight of a high-density polyethylene having a density of 0.955 to 0.970 g/cm$^3$;

(6) The multilayer film according to any one of the above items (1) to (5), wherein the polypropylene used in the 3rd layer has a melt flow rate of 1 to 40 g/10 min. (230° C.) and a melting point of 140 to 170° C.;

(7) The multilayer film according to any one of the above items (1) to (6), wherein a proportion of a thickness of each layer is within the following range:
1st layer: 5 to 15%,
2nd layer: 25 to 45%,
3rd layer: 3 to 15%,
4th layer: 25 to 45%, and
5th layer: 7 to 20%, based on the total thickness of the film;

(8) The multilayer film according to the above item (7), wherein the total thickness of the film is from 200 to 300 μm;

(9) A container which is obtained by molding the multilayer film of any one of the above items (1) to (8), said container comprising the 1st layer of this multilayer film as an outer layer and the 5th layer as an inner layer; and

(10) The container according to the above item (9), which is obtained by interposing a polyethylene port member between the films and welding the port member with the films.

BRIEF DESCRIPTION OF THE DRAWINGS

FIG. 3 is a front view showing another embodiment with respect to the container of the present invention.

Figure 1:
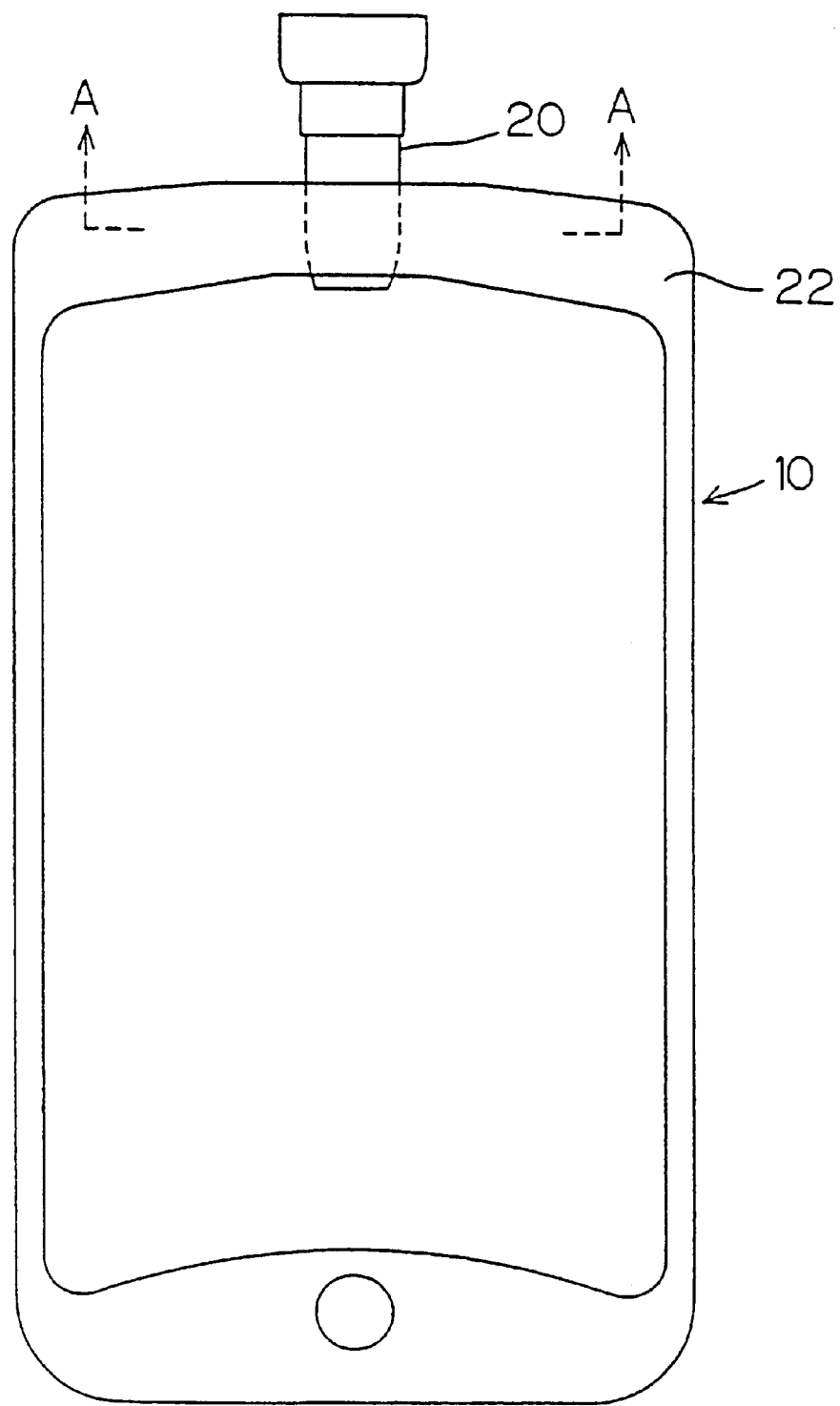
FIG. 1 is a front view showing one embodiment of the container of the present invention.
Figure 2:
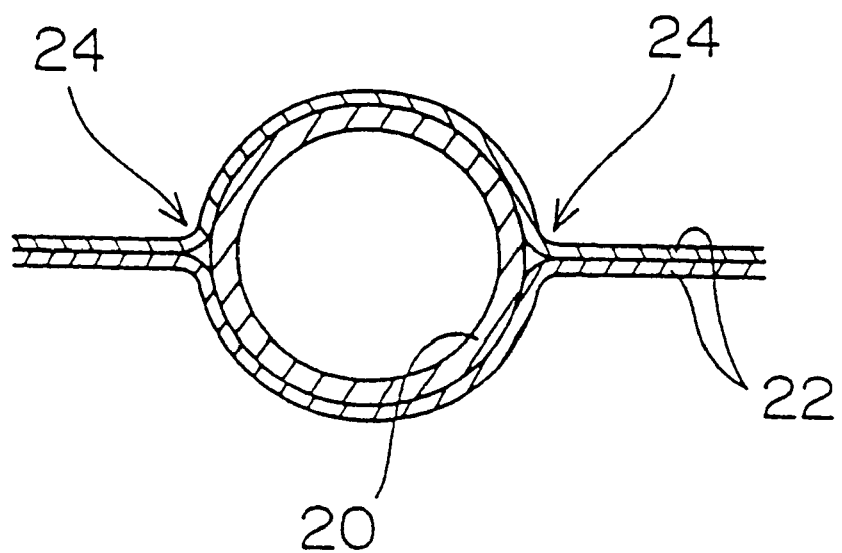
FIG. 2 is a fragmentary cross sectional view taken along lines A—A of FIG. 1.

In the respective drawings, both numeral symbols 10 and 12 denote a container.

BEST MODE FOR CARRYING OUT THE INVENTION

According to the multilayer film of the present invention, since a polypropylene having the heat resistance better than that of the ethylene-α-olefin copolymer is used in the 3rd layer (intermediate layer), the heat resistance of the whole film is improved. Accordingly, it is possible to prevent pinhole from arising when the above medical container (infusion fluid bag) 10 is produced. Particularly, since heat welding of the port 20 can be performed at comparatively high temperature and the film is not excessively stretched at the bending portion 24, it is possible to prevent pinhole from arising at the portion.

In the multilayer film of present invention, the resin used in the 5th layer may be a mixed resin obtained by mixing an ethylene-α-olefin copolymer having a density of 0.915 to 0.950 g/cm$^3$ with a polypropylene having a density of 0.900 to 0.930 g/cm$^3$ in a weight ratio of 1:3 to 9:1.

Also, in the multilayer film of the present invention, the resin used in the 3rd layer may be a mixed resin obtained by mixing a polypropylene having a density of 0.900 to 0.930 g/cm$^3$ with not more than 60% by weight, preferably 5–20% by weight of an ethylene-α-olefin copolymer having a density of 0.860 to 0.930 g/cm$^3$.

Furthermore, in the multilayer film of the present invention, the resin used in the 2nd layer and 4th layer may be a mixed resin comprising 30–60% by weight of an ethylene-α-olefin copolymer having a density of 0.910 to 0.930 g/cm$^3$, 35–65% by weight of an ethylene-α-olefin copolymer having a density of 0.860 to 0.900 g/cm$^3$ and 1–10% by weight of a high-density polyethylene having a density of 0.955 to 0.970 g/cm$^3$.

Also, in the multilayer film of the present invention, the polypropylene used in the 3rd layer preferably has a melt flow rate of 1 to 40 g/10 min. (230° C.) and a melting point of 140 to 170° C.;

In the multilayer film of the present invention, wherein a proportion of a thickness of each layer is preferably within the following range:
1st layer: 5 to 15%,
2nd layer: 25 to 45%,
3rd layer: 3 to 15%,
4th layer: 25 to 45%, and
5th layer: 7 to 20%, based on the total thickness of the film.

It is suitable that the total thickness of the film is from 200 to 300 μm.

Furthermore, the medical container of the present invention is characterized in that it is obtained by molding the multilayer film of any one of the above items (1) to (8), said container comprising the 1st layer of this multilayer film as an outer layer and the 5th layer as an inner layer.

Regarding the multilayer film and container of the present invention, not only the heat resistance is improved, but also the blocking resistance, strength (particularly; tensile strength), sealability and transparency are improved and pinhole can also be prevented.

The resin of each layer in the multilayer film and container of the present invention as well as the method of producing the multilayer film and container of the present invention will be described in detail hereinafter.

All of physical properties defined in the present invention are based on the provision of The American Society for Testing and Materials (ASTM). For example, the density, melt flow rate (MFR) and melting point were measured according to ASTM D1505, ASTM D1238 and ASTM D2117, respectively.

Examples of the ethylene-α-olefin copolymer used in the present invention include copolymers of an α-olefin having 3 to 12 carbon atoms, such as propylene, 1-butene, 1-pentene, 1-hexene, 4-methyl-1-pentene, 1-heptene, 1-octene, 1-nonene, 1-decene, 1-undecene, 1-dodecene or the like, and ethylene. Among them, those having a short-chain as a branched chain, produced by the moderate/low pressure method, are preferably used.

Re 1st Layer:

Since the 1st layer requires the mechanical strength (particularly, tensile strength) and heat resistance, an ethylene-α-olefin copolymer having a density of 0.930 to 0.950 g/cm$^3$, preferably 0.935 to 0.945 g/cm$^3$, is used. Among them, those having MFR of 1.0 to 5.0 g/10 min. (at 190° C.) and a melting point of 120 to 130° C. are used, more suitably. The thickness of the 1st layer is preferably adjusted within the range from 5 to 15% based on the total thickness of the multilayer film.

Re 2nd and 4th Layers:

To impart high flexibility to the film and container, an ethylene-α-olefin copolymer having a density of 0.890 to 0.920 g/cm$^3$ is used in the 2nd and 4th layers. Among them, those having a melting point of 120 to 130° C. are used, more suitably.

A mixture of two or more resins can be used in these 2nd and 4th layer. For example, when using a mixed resin containing (1) 30–60% by weight of an ethylene-α-olefin copolymer having a density of 0.910 to 0.930 g/cm$^3$, (2) 35–65% by weight of an ethylene-α-olefin copolymer having a density of 0.860 to 0.900 g/cm$^3$ and (3) 1–10% by weight of a high-density polyethylene having a density of 0.955 to 0.970 g/cm$^3$, respectively, the heat resistance can be improved without lowering the flexibility of the film.

Among the above ethylene-α-olefin copolymer (1), those having a density of 0.915 to 0.925 g/cm$^3$, MFR of 1.0 to 5.0 g/10 min. (190° C.) and a melting point of 115 to 125° C. are preferable. Among the above ethylene-α-olefin copolymer (2), those having a density of 0.870 to 0.890 g/cm$^3$ and MFR of 0.1 to 2.0 g/10 min. (190° C.) are preferable. The high-density polyethylene (3) may be a homopolymer, or a copolymer of polyethylene and a α-olefin. MFR is preferably from 1 to 30 g/10 min. (190° C.). Regarding the mixing proportion of the above components (1) to (3), the proportion of the component (1), that of the component (2) and that of the component (3) are suitably adjusted within the range from 35 to 55% by weight, 40 to 60% by weight and 3 to 8% by weight, respectively, When using the mixed resin, the density of the whole resin of the 2nd and 4th layers is adjusted within the range from 0.890 to 0.920 g/cm$^3$.

The thickness of the above 2nd and 4th layers is preferably adjusted within the range from 25 to 45% based on the total thickness of the multilayer film. Thus, by providing the above 2nd and 4th layers, the flexibility (elasticity) of the whole film can be maintained, thereby making it possible to maintain the strength of the whole film.

Re 3rd layer:

To maintain the heat resistance, a polypropylene having a density of 0.900 to 0.930 g/cm$^3$ can be used in the 3rd layer. The polypropylene may be a copolymer containing a small amount (generally not more than 10% by weight) of α-olefin such as ethylene, 1-butene or the like, in addition to a homopolymer of propylene.

The polypropylene (or copolymer of α-olefin) is preferably an isotactic polymer having MFR of 1 to 40 g/10 min. (at 230° C.) and a melting point of 140 to 170° C., more preferably an isotactic polymer having MFR of 1 to 7 g/10 min. (at 230° C.) and a melting point of 150 to 170° C.

In the 3rd layer, there can also be used a mixed resin obtained by mixing the above polypropylene with not more than 60% by weight, preferably 5–20% by weight, of an ethylene-α-olefin copolymer having a density of 0.860 to 0.930 g/cm$^3$. As the ethylene-α-olefin copolymer having a density of 0.860 to 0.930 g/cm$^3$, the ethylene-α-olefin copolymer of the above component (1) or (2) used when a mixed resin is used in the above 2nd and 4th layers, or a mixed resin of them can be used.

The thickness of the 3rd layer is preferably adjusted within the range from 3 to 15% based on the whole thickness of the multilayer film.

Re 5th layer:

To maintain the sealability and blocking resistance, an ethylene-α-olefin copolymer having a density of 0.915 to 0.950 g/cm$^3$ is used in the 5th layer. Among them, those having a density of 0.925 to 0.935 g/cm$^3$, MFR of 1.0 to 5.0/10 min. (at 190° C.) and a melting point of 120 to 130° C. are used, more suitably.

When a container having plural (two or more) chambers is produced, since a releasable seal is required at the position where the respective chambers are partitioned off, it is preferable to use a mixed resin containing an ethylene-α-olefin copolymer having a density of 0.915 to 0.950 g/cm$^3$ and a polypropylene having a density of 0.900 to 0.930 g/cm$^3$ in a weight ratio of 1:3 to 9:1, preferably 2:1 to 7:1. Examples of the polypropylene used in such a mixed resin include the same one as that used in the 3rd layer.

The thickness of the 5th layer is preferably adjusted within the range from 7 to 20% based on the total thickness of the multilayer film. Since all resins of the 1st to 5th layers have high transparency, the transparency of the whole film is also good.

When the multilayer film of the present invention is used, there can be used water-cooling or air-cooling type coextrusion inflation method, coextrusion T-die method, dry lamination method, extrusion lamination method or the like. In view of the performances (particularly transparency), economical efficiency and sanitation, the water-cooling coextrusion inflation method and coextrusion T-die method are preferably used. In both methods, the production must be performed at the temperature at which the resin of each layer is molten. When the temperature is too raised, a part of the resin is thermally decomposed and deterioration of the performances are liable to be caused by the decomposition product. Accordingly, the temperature at the time of producing the multilayer film of the present invention is normally adjusted within the range from 150 to 250° C., preferably from 170 to 200° C. The smaller a difference in MFR between the resin constituting each layer, the better in order to maintain the transparency.

The thickness of the film of the present invention thus produced as described above is normally from 100 to 350 μm, preferably from 200 to 300 μm, but can be appropriately adjusted according to the purpose. Even if the thickness is about 250 μm, the film has sufficient strength.

The container of the present invention will be described hereinafter with reference to FIG. 1 and FIG. 3, which respectively show one embodiment of the container.

FIG. 1 is a front view showing a single-chamber medical container (infusion liquid bag) 10. Regarding the single-chamber 10, a container 10 having a predetermined shape and size is produced by cutting the above resulting two sheet-like multilayer films using a normal method, piling up them together with each 5th layer as the inner layer, heat-sealing peripheries of the container 10, and attaching a port member 20 using a means such as heat sealing. The container 10 may be produced by heating sealing after molding the 5th layer of the multilayer film into a tube while the 5th layer being inside. As the conditions of heat sealing of the film, the temperature ranging from 130 to 200° C. can be used. For example, in the case of a film having a thickness of about 250 μm, sealing can be performed within a short time (about 0.5 to 6 sec.) within the above temperature range.

As the port member 20, those obtained by molding a resin having excellent weldability with the 5th layer in the multilayer film of the present invention, e.g. polyethylene, etc. are preferably used. As the conditions of heat sealing in the case of the port member 20 made of polyethylene having a melting point of about 120 to 130, the port member may be heated at about 140 to 170° C. for about 0.5 to 5 seconds after previous heating for a few seconds.

FIG. 3 is a front view showing a medical container (infusion liquid bag) 12 having plural chambers for containing a liquid medicine (this figure showing the example of two chambers). Regarding this medical container 12 having plural chambers, containing chambers 14, 16 for containing different kinds of liquid medicines, respectively, are partitioned off with a weak sealing portion 18. When using the container, the weak sealing portion 18 is broken by means of a liquid pressure, thereby to mix the liquid medicines.

The medical container 12 having plural chambers is produced in the same manner as that of a single-chamber medical container 10, but the temperature of heat sealing is set at the temperature lower than that of the peripheral portion when the weak sealing portion 18 for partitioning the containing chambers 14, 16. As the conditions of heat sealing of the weak sealing portion 14, heating may be normally performed at about 120 to 150° C. for about 3 to 6 seconds.

When the medical container 12 having plural chambers is produced, the 5th layer of the multilayer film is preferably a mixed resin obtained by mixing an ethylene-α-olefin copolymer having a density of 0.915 to 0.950 g/cm³ with a polypropylene having a density of 0.900 to 0.930 g/cm³ in a weight ratio of 1:3 to 9:1. By using such a mixed resin, the sealability of the weak sealing portion 18 can be controlled so that a strength suited to peel off by the liquid pressure can be obtained.

In the medical container 12 having plural chambers, the conditions of heating sealing of the port member 20 are the same as those described above.

EXAMPLES

Examples 1 to 5
(Production of Multilayer Film)

A film having a layer construction shown in the following Table 1 was molded by the water-cooling coextrusion inflation method, respectively.

The resins A to E shown in Table 1 are as follows.

A: Ethylene-1-butene copolymer [manufactured by Mitsui Kagaku Co., Ltd., density=0.940 g/cm³, MFR=2.1 g/10 min. (190° C.)]

B: Mixed resin (density of mixed resin=0.906 g/cm³) of the following components (a) to (c)
   (a) Ethylene-1-butene copolymer [manufactured by Mitsui Kagaku Co., Ltd., density=0.920 g/cm³, MFR=2.1 g/10 min. (190° C.)], 45% by weight
   (b) Ethylene-1-butene copolymer elastomer [manufactured by Mitsui Kagaku Co., Ltd., density= 0.885 g/cm³, MFR=0.5 g/10 min. (190° C.)], 50% by weight
   (c) Ethylene-1-butene copolymer [manufactured by Mitsui Kagaku Co., Ltd., density=0.962 g/cm³, MFR=15 g/10 min. (190° C.)], 5% by weight C: Isotactic polypropylene (content of ethylene: not more than 5% by weight) [manufactured by Mitsui Kagaku Co., Ltd., density=0.910 g/cm³, MFR=1.6 g/10 min. (230° C.)]

D: Ethylene-1-butene copolymer [manufactured by Mitsui Kagaku Co., Ltd., density=0.930 g/cm³, MFR=2.1 g/10 min. (190° C.)]

E: Mixed resin (density of mixed resin=0.927 g/cm³) comprising 86% by weight of the resin D and 14% by weight of an isotactic polypropylene (homopolymer) [manufactured by Mitsui Kagaku Co., Ltd., density= 0.910 g/cm³, MFR=4.0 g/10 min. (230° C.)]

F: Mixed resin comprising 45% by weight of an isotactic polypropylene (content of ethylene: not more than 5% by weight) [manufactured by Mitsui Kagaku Co., Ltd., density=0.910 g/cm³, MFR=40 g/10 min. (230° C.)] and 55% by weight of an ethylene-1-butene copolymer [manufactured by Mitsui Kagaku Co., Ltd., density= 0.920 g/cm³, MFR=2.1 g/10 min. (190° C.)]

G: Mixed resin (density of mixed resin=0.905 g/cm³) comprising 45% by weight of the resin (a), 50% by weight of the resin (b) and 5% by weight of a polyethylene homopolymer [manufactured by Mitsui Kagaku Co., Ltd., density 0.965 g/cm³, MFR=15 g/10 min. (190° C.)]

H: Mixed resin comprising 90% by weight of an isotactic polypropylene (content of ethylene: not more than 5% by weight) [manufactured by Mitsui Kagaku Co., Ltd., density=0.900 g/cm³, MFR=1.1 g/10 min. (230° C.)] and an ethylene-1-butene copolymer [manufactured by Mitsui Kagaku Co., Ltd., density=0.885 g/cm³, MFR= 3.6 g/10 min. (190° C.)]

I: Mixed resin comprising 85% by weight of the resin A and 15% by weight of an isotactic polypropylene (homopolymer) [manufactured by Mitsui Kagaku Co., Ltd., density=0.910 g/cm³, MFR=4.0 g/10 min. (230° C.)]

TABLE 1

|  | FIRST LAYER | SECOND LAYER | THIRD LAYER | FOURTH LAYER | FIFTH LAYER |
| --- | --- | --- | --- | --- | --- |
| EXAMPLE 1 | A | B | C | B | D |
|  | 20 μm | 90 μm | 20 μm | 90 μm | 40 μm |
| EXAMPLE 2 | A | B | C | B | E |
|  | 25 μm | 95 μm | 15 μm | 95 μm | 30 μm |
| EXAMPLE 3 | A | B | F | B | D |
|  | 20 μm | 90 μm | 20 μm | 90 μm | 40 μm |
| EXAMPLE 4 | A | B | H | G | I |
|  | 20 μm | 94 μm | 18 μm | 94 μm | 30 μm |
| EXAMPLE 5 | A | B | H | G | D |
|  | 20 μm | 94 μm | 18 μm | 94 μm | 30 μm |

A TO H: KIND OF RESIN
NUMERICAL VALUES: THICKNESS (μm)

(Production of Container)

Using the films of Examples 1, 3 and 5, a single-chamber medical container (infusion liquid bag) 10 having an internal volume of 500 ml was produced, respectively. Heat sealing in case of molding this medical container 10 was performed at 145° C. for 4.5 seconds, whereas sealing of a port member 20 was performed at 145° C. for 3 seconds.

Using the film of Examples 2 and 4, a medical container (infusion liquid bag) 12 having plural chambers and an internal volume of 900 ml was produced. Heat sealing in the case of molding this medical container 12 was performed at 185° C. for 4.5 seconds, whereas heat sealing of a weak sealing portion 14 was performed at 135° C. for 4.5 seconds and sealing of a port member 20 was performed at 160° C. for 3 seconds.

As the port member 20 used in the above medical containers 10, 12, those made of an ethylene-1-butene copolymer having a density of 0.945 cm and a melting point of about 128° C. were used after heating at about 740° C. using a heater before sealing.

(Test Examples)

With respect to the medical containers (infusion bag) 10, 12 obtained by using the multilayer films of Examples 1 to 5, the evaluation test of various characteristics and examination of pinhole were performed by using the following methods.

Heat resistance: A container was filled with distilled water and subjected to high-pressure steam sterilization at 110° C. for 40 minutes. Then, the state of deformation, breakage and seal leakage of the container was visually observed.

Drop test: After refrigerating at 4° C., a container was dropped from the height of 1 m in three directions five times, respectively. The state of breakage and seal leakage was visually observed.

Flexibility: The natural discharging property of the internal liquid was visually observed.

Transparency: A container was filled with distilled water and subjected to high-pressure steam sterilization in the same manner as that described above. Then, the state of the container was visually observed and, furthermore, the light transmission at 450 nm was measured.

Appearance: It was visually observed, and the state of crease, blocking, deformation and breakage was examined.

In the evaluation of the above heat resistance, drop test, flexibility, transparency and appearance, the symbols "⊙", "○", "Δ" and "x" denote "Excellent", "Good", "Slightly Poor" and "Poor", respectively.

Examination of Pinhole

After three thousand of medical containers (infusion fluid bag) were filled with physiological saline and then sealed with a rubber stopper, the presence or the absence of pinhole at the sealed portion of the port 20 was examined by using a simple electrostatic capacity type pinhole tester at an applied voltage of 15 kV.

The above test results are shown in Table 2.

TABLE 2

| | EXAMPLE 1 | EXAMPLE 2 | EXAMPLE 3 | EXAMPLE 4 | EXAMPLE 5 |
|---|---|---|---|---|---|
| HEAT RESISTANCE | ⊙ | ○ | ⊙ | ⊙ | ⊙ |
| DROP TEST | ⊙ | ⊙ | ⊙ | ⊙ | ⊙ |
| FLEXIBILITY | ⊙ | ⊙ | ⊙ | ⊙ | ⊙ |
| TRANSPARENCY | | | | | |
| VISUAL OBSERVATION | ⊙ | ⊙ | ⊙ | ⊙ | ⊙ |
| TRANSMISSION (%) | 83.2 | 82.7 | 80.5 | 82.5 | 82.3 |
| APPEARANCE | ⊙ | ⊙ | ⊙ | ⊙ | ⊙ |
| PINHOLE | NONE | NONE | NONE | NONE | NONE |

As is apparent from the results of Table 2, the container of the present invention showed good results in any item of heat resistance, drop test, flexibility, transparency and appearance. In the examination of pinhole, any defective products with pinhole were not observed.

According to the same manner as that described in Examples 1 to 5, films having the layer construction shown in the following Table 3 can also be molded. These films also have the same excellent properties as those described above.

Among the resins shown in Table 3, J to N are as follows.

J: Ethylene-1-butene copolymer [manufactured by Mitsui Kagaku Co., Ltd., density=0.945 g/cm$^3$, MFR=10 g/10 min. (190° C.)]

K: Ethylene-1-butene copolymer [manufactured by Mitsui Kagaku Co., Ltd., density=0.895 g/cm$^3$, MFR=1.0 g/10 min. (190° C.)]

L: Mixed resin (density of the mixed resin=0.915 g/cm$^3$) comprising 55% by weight of the resin (a), 35% by weight of the resin K and 10% by weight of the resin (c)

M: Mixed resin comprising 85% by weight of the resin J and 15% by weight of an isotactic polypropylene (homopolymer) [manufactured by Mitsui Kagaku Co., Ltd., density=0.910 g/cm$^3$, MFR=4.0 g/10 min. (230° C.)]

N: Mixed resin comprising 85% by weight of the resin (a) and 15% by weight of an isotactic polypropylene (homopolymer) [manufactured by Mitsui Kagaku Co., Ltd., density=0.910 g/cm$^3$, MFR=4.0 g/10 min. (230° C.)]

TABLE 3

| No. | FIRST LAYER | SECOND LAYER | THIRD LAYER | FOURTH LAYER | FIFTH LAYER |
|---|---|---|---|---|---|
| 6 | J | K | C | K | J |
|   | 15 μm | 95 μm | 35 μm | 95 μm | 20 μm |
| 7 | J | K | H | K | J |
|   | 15 μm | 95 μm | 35 μm | 95 μm | 20 μm |
| 8 | D | L | C | L | (a) |
|   | 35 μm | 85 μm | 10 μm | 85 μm | 50 μm |
| 9 | J | K | C | K | M |
|   | 15 μm | 95 μm | 35 μm | 95 μm | 20 μm |
| 10 | D | L | C | L | N |
|   | 35 μm | 85 μm | 10 μm | 85 μm | 50 μm |

(a), C, D and J TO N: KIND OF RESIN
NUMERICAL VALUES: THICKNESS (μm)

INDUSTRIAL APPLICABILITY

The multilayer film and container of the present invention are superior in heat resistance, blocking resistance, strength, sealability, transparency, flexibility and appearance, and have such an advantage that pinhole do not arise at the bending portion at the time of heat sealing. Therefore, the multilayer film and container of the present invention can be suitably used as a medical container such as infusion fluid bag, blood bag or the like.

The disclosure of Japanese Patent Application Serial No.9-192765, filed on Jul. 17, 1997, is incorporated herein by reference.

What is claimed is:

1. A multilayer film comprising five layers, wherein each layer is constituted by a resin having the following density in that order:

1st layer: an ethylene-α-olefin copolymer having a density of 0.930 to 0.950 g/cm$^3$, 2nd layer: an ethylene-α-olefin copolymer having a density of 0.890 to 0.920 g/cm$^3$, 3rd layer: a polypropylene having a density of 0.900 to 0.930 g/cm$^3$, 4th layer: an ethylene-α-olefin copolymer having a density of 0.890 to 0.920 g/cm$^3$, and 5th layer: an ethylene-α-olefin copolymer having a density of 0.915 to 0.950 g/cm$^3$.

2. The multilayer film according to claim 1, wherein the resin used in the 5th layer is a mixed resin obtained by mixing an ethylene-α-olefin copolymer having a density of 0.915 to 0.950 g/cm$^3$ with a polypropylene having a density of 0.900 to 0.930 g/cm$^3$ in a weight ratio of 1:3 to 9:1.

3. The multilayer film according to claim 1, wherein the resin used in the 3rd layer is a mixed resin obtained by mixing a polypropylene having a density of 0.900 to 0.930 g/cm$^3$ with not more than 60% by weight of an ethylene-α-olefin copolymer having a density of 0.860 to 0.930 g/cm$^3$.

4. The multilayer film according to claim 3, wherein the resin used in the 3rd layer is a mixed resin obtained by mixing a polypropylene having a density of 0.900 to 0.930 g/cm$^3$ with 5–20% by weight of an ethylene-α-olefin copolymer having a density of 0.860 to 0.930 g/cm$^3$.

5. The multilayer film according to any one of claims 1 to 4, wherein the resin used in the 2nd layer and 4th layer is a mixed resin comprising 30–60% by weight of an ethylene-α-olefin copolymer having a density of 0.910 to 0.930 g/cm$^3$, 35–65% by weight of an ethylene-α-olefin copolymer having a density of 0.860 to 0.900 g/cm$^3$ and 1–10% by weight of a high-density polyethylene having a density of 0.955 to 0.970 g/cm$^3$.

6. The multilayer film according to any one of claim 1, wherein the polypropylene used in the 3rd layer has a melt flow rate of 1 to 40 g/10 min. (230° C.) and a melting point of 140 to 170° C.

7. The multilayer film according to any one of claim 1, wherein a proportion of a thickness of each layer is within the following range:

1st layer: 5 to 15%,

2nd layer: 25 to 45%,

3rd layer: 3 to 15%,

4th layer: 25 to 45%, and

5th layer: 7 to 20%, based on the total thickness of the film.

8. The multilayer film according to claim 7, wherein the total thickness of the film is from 200 to 300 μm.

9. A container which is obtained by molding using the multilayer film of any one of claim 1, said container comprising the 1st layer of this multilayer film as an outer layer and the 5th layer as an inner layer.

10. The container according to claim 9, which is obtained by interposing a polyethylene port member between the films and welding the port member with the films.

* * * * *